(12) United States Patent
Al-Hussain et al.

(10) Patent No.: US 10,428,645 B2
(45) Date of Patent: *Oct. 1, 2019

(54) INTEGRATED METHOD OF DETERMINING AND REPAIRING DAMAGE IN A WELL CASING

(71) Applicant: KING FAHD UNIVERSITY OF PETROLEUM AND MINERALS, Dhahran (SA)

(72) Inventors: Ali Musa Al-Hussain, Dhahran (SA); M. Enamul Hossain, Dhahran (SA)

(73) Assignee: King Fahd University of Petroleum and Minerals, Dhahran (SA)

( * ) Notice: Subject to any disclaimer, the term of this patent is extended or adjusted under 35 U.S.C. 154(b) by 0 days.

This patent is subject to a terminal disclaimer.

(21) Appl. No.: 16/151,919

(22) Filed: Oct. 4, 2018

(65) Prior Publication Data

US 2019/0032478 A1    Jan. 31, 2019

Related U.S. Application Data

(63) Continuation of application No. 15/079,157, filed on Mar. 24, 2016, now Pat. No. 10,125,602.

(51) Int. Cl.
*E21B 47/10*    (2012.01)
*E21B 47/06*    (2012.01)
*G01B 21/08*    (2006.01)
*G01N 17/04*    (2006.01)

(52) U.S. Cl.
CPC ........ *E21B 47/1015* (2013.01); *E21B 47/065* (2013.01); *E21B 47/10* (2013.01); *E21B 47/101* (2013.01); *E21B 47/1005* (2013.01); *G01B 21/08* (2013.01); *G01N 17/04* (2013.01)

(58) Field of Classification Search
CPC ........................................... E21B 47/10
USPC ............................................. 702/6
See application file for complete search history.

(56) References Cited

U.S. PATENT DOCUMENTS

| | | |
|---|---|---|
| 4,109,717 A | 8/1978 | Cooke, Jr. |
| 4,114,721 A | 9/1978 | Glenn, Jr. |
| 5,353,873 A | 10/1994 | Cooke, Jr. |
| 5,509,474 A | 4/1996 | Cooke, Jr. |
| 6,098,020 A | 8/2000 | Den Boer |
| 7,380,598 B2 | 6/2008 | Wydrinski et al. |
| 8,408,064 B2 | 4/2013 | Hartog et al. |
| 2009/0243604 A1* | 10/2009 | Dutta ............... G01B 7/10 324/229 |
| 2013/0255940 A1 | 10/2013 | Rochford |

(Continued)

OTHER PUBLICATIONS

East West Energy Services Ltd., "TecWell Well Leak Detector (WLD)", URL: http://www.ewesl.com/Product_WLD.html, Total 1 Page, (2007).

*Primary Examiner* — Moazzam Hossain
*Assistant Examiner* — Omar F Mojaddedi
(74) *Attorney, Agent, or Firm* — Oblon, McClelland, Maier & Neustadt, L.L.P.

(57) ABSTRACT

An integrated and rigless method of determining the location and the type of damage in casing or tubing of a wellbore that involves recording a thickness profile of the casing or tubing, a temperature log, and a noise log along the depth of the wellbore, followed by locating the damage from the thickness profile, and determining the type of damage from the temperature log and the noise log.

8 Claims, 4 Drawing Sheets

(56) References Cited

U.S. PATENT DOCUMENTS

2017/0299758 A1    10/2017  Pelletier
2017/0350234 A1*   12/2017  Xia ......................... E21B 47/06

* cited by examiner

INTEGRATED METHOD OF DETERMINING AND REPAIRING DAMAGE IN A WELL CASING

CROSS-REFERENCE TO RELATED APPLICATIONS

The present application is a Continuation of Ser. No. 15/079,157, now allowed, having a filing date of Mar. 24, 2016.

TECHNICAL FIELD

The present invention relates to an integrated method of determining the location and the type of damage in casing or tubing of a wellbore. The method involves recording a thickness profile, a temperature log, and a noise log along the well, and further locating the damage from the thickness profile, along with determining the type of damage from the temperature log and the noise log.

DESCRIPTION OF THE RELATED ART

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

Effective well integrity practices ensure the protection of people, facilities and the environment from the risk of uncontrolled release of formation fluids throughout the life cycle of a well, so petroleum engineers are always required to ensure well integrity. Part of well integrity is to make sure downhole equipment and barriers are in excellent condition. Discovering the downhole leak source of pressure communication between tubing-casing and casing-casing annuli in any well, particularly at early stages, is a huge challenge for the oil industry and the key to well integrity management.

Subsurface well integrity is important for any type of well to avoid the risk of uncontrolled release of formation fluids throughout the life cycle of that well which is necessary for both protecting the environment and health of people. The currently employed techniques to locate well anomalies is not sufficiently reliable, therefore, a reliable methodology is needed to identify any small source of downhole leaks.

Thickness profile (or thickness log) offers valuable visions to ensure the effective application of safety and environmental regulations. Thickness profile can be obtained by a mechanical caliper tool which is used to detect the internal condition of a pipe (e.g. tubing or casing). Its log results are affected by scale build up on the internal wall. Thickness profile can also be obtained by an electromagnetic tool which is used to detect a pipe inner diameter and to compare it with the actual inner pipe diameter. It consists of transmitters and receivers to generate the thickness profiles. Thickness profile can also be obtained by an ultrasonic acoustic tool. The tool generates high frequency ultrasonic pulses through a pipe (e.g. tubing or casing) wall. The amplitude and travel time of echoes are used to generate a thickness profile. Thickness profile can be used to locate damage zones in the tubing and/or casing, or to evaluate the condition of tubing and/or casing.

Temperature log is one of the reliable logs for leak detection. The classical procedure is to obtain a true geothermal temperature profile and correlate future temperature changes to the geothermal temperature profile to obtain an estimate of the location, magnitude and direction of the cross-flow anomalies. It indicates the presence of flow from its static or geothermal value. Under static conditions, temperature increases gradually with depth. The nature of well completion also influences the method in which temperature returns to its geothermal value. A good knowledge of the geothermal gradient is necessary for having representative interpretation. Interpretation of temperature logging was observed for flow measurements and studied by Nowak in 1953. In 1969 and 1979, Cocanwer and Romero-Juarez respectively have provided similar approaches. The purpose of temperature log is to identify any cross flow and abnormal geothermal phenomena.

Noise log is a record of a passive measure of the noticeable sound detected by sensitive hydrophones at a number of locations in the wellbore. It is designed to record sounds in specific frequency range based on the design tool. In 1955 Enright introduced noise log as a qualitative indicator of channeling behind pipe. This concept describes the procedure of locating tubing and casing leaks with acoustic recorder which detect the highest noise level at leaks. In 1970 Korotaev used a noise detector to identify gas bearing zones in uncased well. In 1994 McKinley introduced a noise logging technology based on the recording of acoustic noise into several frequency channels and presented the results of his own experimental research. Later on with noise technology development, noise log started to be used quantitatively to estimate flow rates in some instances, and its application has been extended beyond channel detection.

In view of the forgoing, one objective of the present invention is to develop an integrated and rigless method for determining location and type of a damage in casing or tubing of a wellbore using thickness profile (or thickness log), temperature log, and noise log.

BRIEF SUMMARY OF THE INVENTION

According to a first aspect, the present disclosure relates to an integrated method of determining location and type of a damage in a casing of a well, involving i) logging thickness of the casing along the depth of the well to obtain a thickness profile, ii) logging temperature along the depth of the well to obtain a temperature log, iii) logging sound frequency along the depth of the well to obtain a noise log, iv) determining the location of the damage by identifying a depth in the thickness profile where the thickness is less than a predetermined thickness threshold, v) determining the type of the damage by comparing the temperature log to a geothermal temperature log, and the sound frequency at the damage with a frequency threshold.

In one embodiment, the damage is determined to be a leak, when the temperature of the temperature log is constant or decreases relative to the geothermal temperature log with increasing depth along the vicinity of the damage.

In one embodiment, the damage is determined to be a leak, when the temperature of the temperature log fluctuates with increasing depth along the vicinity of the damage, and the sound frequency is greater than or equal to the frequency threshold in the vicinity of the damage.

In one embodiment, the damage is determined to be corrosion, when the temperature of the temperature log increases relative to the geothermal temperature log with increasing depth along the vicinity of the damage.

In one embodiment, the damage is determined to be corrosion, when the temperature of the temperature log fluctuates with increasing depth along the vicinity of the damage, and the sound frequency is less than the frequency threshold in the vicinity of the damage.

In one embodiment, the damage has at least one crack and the method further comprises determining the depth of the at least one crack by measuring amplitude and travel time of reflected sonic signals in the vicinity of the damage.

In one embodiment, the thickness is logged by a thickness measurement device selected from the group consisting of a mechanical caliper, an ultrasonic caliper, an electromagnetic caliper, and a flux-leakage tool.

In one embodiment, the temperature is logged by at least one temperature sensor selected from the group consisting of a thermocouple, a resistance temperature detector, a thermistor, and a silicon bandgap temperature sensor.

In one embodiment, the noise log further comprises sound level, and the sound level and the sound frequency in the noise log are obtained by a submersible noise detector.

In one embodiment, the well further comprises tubing which is located concentrically inside the casing, and the method determines the location and type of damage in the tubing.

In one embodiment, the casing is selected from the group consisting of a conductor casing, a surface casing, an intermediate casing, and a production casing.

In one embodiment, the integrated method is a rigless operation.

In one embodiment, a subterranean formation surrounds the well, and the subterranean formation comprises one or more of natural gas, oil, gas condensate, and water.

According to a second aspect, the present disclosure relates to a non-transitory computer readable medium having instructions stored therein that, when executed by a computer, cause the computer to perform an integrated method of determining location and type of a damage in a casing of a well, the integrated method involves i) logging thickness of the casing along the depth of the well to obtain a thickness profile, ii) logging temperature along the depth of the well to obtain a temperature log, iii) logging sound frequency along the depth of the well to obtain a noise log, iv) determining the location of the damage by identifying a depth in the thickness profile where the thickness is less than a predetermined thickness threshold, v) determining the type of the damage by comparing the temperature log to a geothermal temperature log, and the sound frequency at the damage with a frequency threshold.

In one embodiment, the non-transitory computer readable medium having instructions stored therein that, when executed by a computer, cause the computer to characterize the damage as leak, when the temperature of the temperature log is constant or decreases relative to the geothermal temperature log with increasing depth along the vicinity of the damage.

In one embodiment, the non-transitory computer readable medium having instructions stored therein that, when executed by a computer, cause the computer to characterize the damage as leak, when the temperature of the temperature log fluctuates with increasing depth along the vicinity of the damage, and the sound frequency is greater than or equal to the frequency threshold in the vicinity of the damage.

In one embodiment, the non-transitory computer readable medium having instructions stored therein that, when executed by a computer, cause the computer to characterize the damage as corrosion, when the temperature of the temperature log increases relative to the geothermal temperature log with increasing depth along the vicinity of the damage.

In one embodiment, the non-transitory computer readable medium having instructions stored therein that, when executed by a computer, cause the computer to characterize the damage as corrosion, when the temperature of the temperature log fluctuates with increasing depth along the vicinity of the damage, and the sound frequency is less than the frequency threshold in the vicinity of the damage.

In one embodiment, the damage has at least one crack and the non-transitory computer readable medium having instructions stored therein that, when executed by a computer, cause the computer to determine the depth of the at least one crack by measuring amplitude and travel time of reflected sonic signals in the vicinity of the damage.

In one embodiment, the thickness profile, the temperature log, and the noise log are measured in parallel in real-time.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein.

DETAILED DESCRIPTION OF THE EMBODIMENTS

Figure 1:
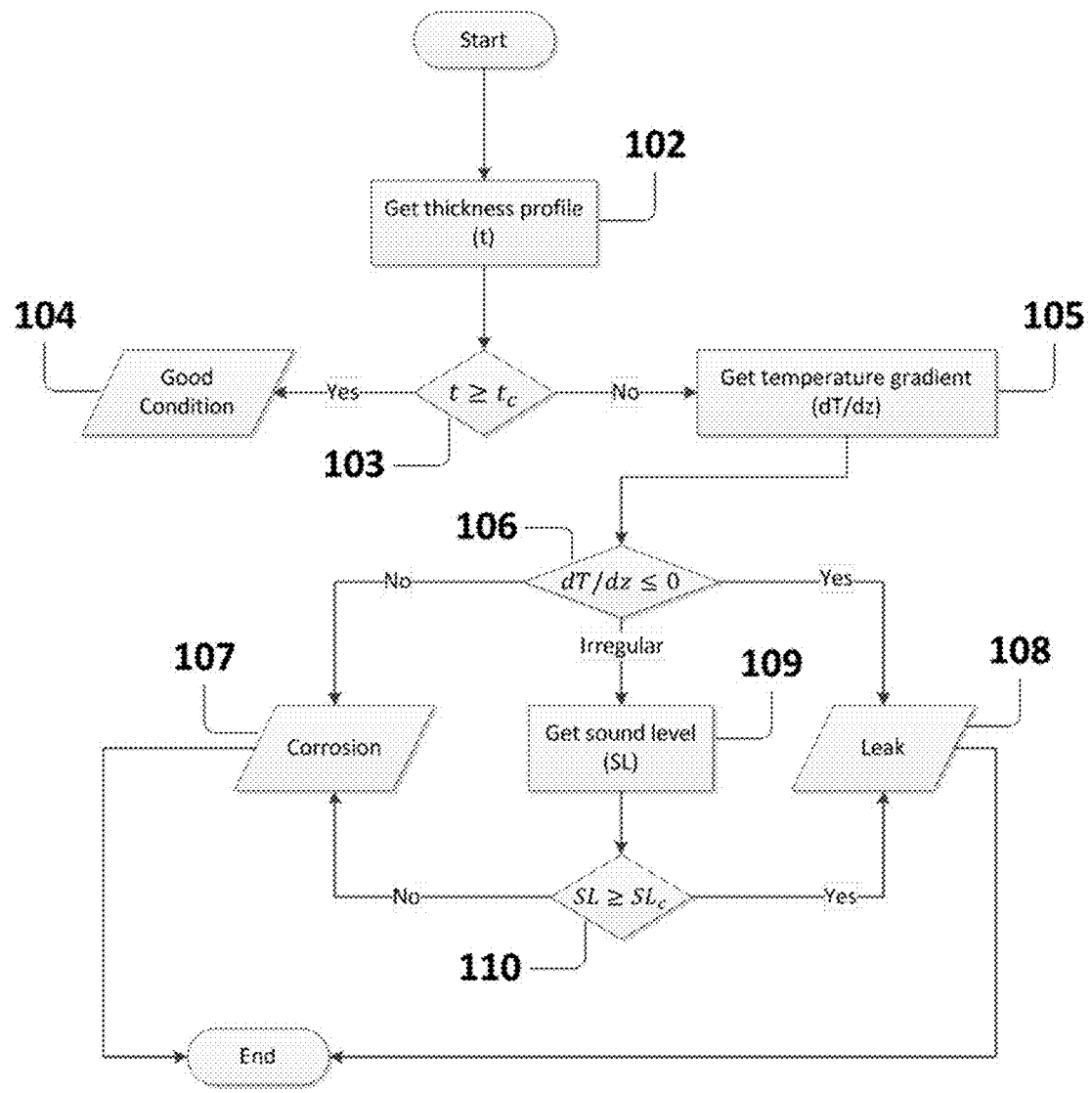
FIG. 1 depicts a flowchart of the non-transitory computer readable medium determining location and type of a damage in a casing or tubing of a well.

Referring now to the drawings, wherein like reference numerals designate identical or corresponding parts throughout the several views.

According to a first aspect, the present disclosure relates to an integrated method of determining location and type of a damage in a casing of a well, involving logging thickness of the casing along the depth of the well to obtain a thickness profile 302.

The well may be a vertical well or a directional well. Exemplary directional wells include, but are not limited to horizontal wells, multilateral wells, extended reach wells, and maximum reservoir contact (MRC) wells. Horizontal wells may be employed to enhance reservoir performance and production by placing a horizontal lateral section within a reservoir to increase a reservoir contact. The horizontal lateral section may have an inclination angle of at least 80°, or at least 85°, or at least 86°, or at least 87°, or at least 88°, or at least 89°, or at least 90° from the central borehole of the well. A multilateral well is a type of directional well wherein several laterals extend outwardly from a main/central borehole. Extended reach well is one type of directional well in which ratio of a measured depth to a true vertical depth (TVD) is at least 2, or at least 5, or at least 10. True vertical depth refers to a vertical distance from a point in the well (usually a current or a final depth) to a point at the surface of the well. Maximum reservoir contact (MRC) well is one type of directional well that provides an aggregate reservoir contact. The aggregate reservoir contact may be provided through a linear penetration through the reservoir of at least 5 km, or at least 6 km, or at least 8 km, through a single or a multi-lateral configuration. The linear penetration may be straight vertical, straight horizontal, zigzag, and/or any combination thereof. "Along the depth" as used herein refers to a path from the surface of the well to the bottom of the well. In one embodiment, along the depth may refer to the path of logging, or logging length. The path may be straight vertical, straight horizontal, zigzag, spiral/helical, curved, wavy, and/or any combination thereof.

"Well" as used herein also refers to "wellbore", and therefore these terms may be used interchangeably.

In one embodiment, a subterranean formation surrounds the well. Subterranean formation refers to a subsurface body of geological formations around a wellbore (i.e. an uncased portion of a well) having sufficient porosity and permeability to store and transfer fluids. A subterranean formation may be a carbonate formation, a sandstone formation, a shale formation, or a clay formation. In one embodiment, the subterranean formation comprises one or more of natural gas, oil, gas condensate, and water.

Casing refers to a pipe which is lowered into a borehole of a well and cemented in place. Casing may often be manufactured from plain carbon steel, aluminum, titanium, fiberglass and other materials. Exemplary casings include, but are not limited to a conductor casing, a surface casing, an intermediate casing, and a production casing. The outer diameter of the casing may be in the range of 50-1,000 mm, or preferably 100-500 mm, or preferably 100-400 mm, or preferably 100-300 mm, or preferably 140-280 mm. Wall thickness (also referred to herein as "thickness") of the casing may be in the range of 1-40 mm, or preferably 5-40 mm, or preferably 5-30 mm, or preferably 5-20 mm. The casing may withstand a variety of forces, such as collapse, burst, and tensile failure, as well as chemically aggressive brines. The casing may have yield strength in the range of 10-200 ksi, or preferably 40-150 ksi, or preferably 80-150 ksi, and an ultimate tensile strength in the range of 50-200 ksi, or preferably 60-150 ksi, or preferably 90-150 ksi. The casing may also have elongation-at-failure in the range of 10-40%, or preferably 15-35%, or preferably 18-30%.

In one embodiment, the well further comprises tubing which may be located concentrically inside the casing. Tubing refers to a conduit through which oil and/or gas are brought from the subterranean formations to the surface of the well. Tubing is generally adequately strong to resist loads and deformations associated with production. Tubing may often be manufactured from plain carbon steel, aluminum, titanium, fiberglass and other materials. The outer diameter of the tubing may be in the range of 50-500 mm, or preferably 50-300 mm, or preferably 50-200 mm, or preferably 60-120 mm. Wall thickness (also referred to herein as "thickness") of the tubing may be in the range of 1-30 mm, or preferably 3-30 mm, or preferably 3-20 mm, or preferably 4-10 mm. The tubing may withstand a variety of forces, such as collapse, burst, and tensile failure, as well as chemically aggressive brines. The tubing may have yield strength in the range of 10-200 ksi, or preferably 40-150 ksi, or preferably 80-150 ksi, and an ultimate tensile strength in the range of 50-200 ksi, or preferably 60-150 ksi, or preferably 90-150 ksi. The tubing may also have elongation-at-failure in the range of 10-40%, or preferably 15-35%, or preferably 18-30%.

Damage as used herein may refer to any imperfection, deformation, and/or distortion in the casing or tubing of a well. Exemplary types of damage in the casing or the tubing include, but are not limited to thinning, metal loss, buckles, fractures, pits, holes, dents, cracks, and leaks. Damage in the casing or tubing of a well can be caused by mechanical deformation, physical wear, and/or corrosion.

In one embodiment, the damage in the casing or tubing of the well is corrosion 203. Corrosion refers to a gradual degradation of materials (usually metals) due to a chemical or an electrochemical reaction with their environment. Corrosion may be caused by a flow of electrons from one material to another or from one part of a material to another part of the material where conditions permit the flow of electrons. Corrosion may occur anywhere in a casing or tubing of a well. Corrosion 203 may lead the thickness of the casing or tubing to become thinner. In one embodiment, corrosion may also cause the formation of leaks in the casing or tubing of the well. Corrosion may also weaken the casing or tubing without an apparent change in thickness, for example, corrosion may cause a lower bursting strength of the casing or tubing. Corrosion may also ease the initiation and propagation of a crack by lowering fracture toughness of the casing or tubing.

In one embodiment, the damage in the casing or tubing of the well is a leak 303. Leak may be formed in the casing or tubing as a result of a severe corrosion caused by a caustic base or a strong corrosive acid. Exemplary corrosive acids include, but are not limited to sulfuric acid, nitric acid, hydrochloric acid, and hydrofluoric acid. Exemplary caustic bases include, but are not limited to sodium hydroxide, potassium hydroxide, and calcium hydroxide. Leak may also be formed in the casing or tubing due to external mechanical stress applied to the casing or tubing.

Logging refers to a continuous in-situ measurement of properties and/or characteristics of geological formations, liquids in the wellbore, casing, and/or tubing followed by recording the continuous in-situ measurement versus time and/or depth of the well. Examples of the in-situ measurements include, but are not limited to geological properties (i.e. permeability, porosity, etc.), electrical properties (i.e. resistivity, conductivity, etc.), sonic properties, dimensional measurements of the wellbore, formation fluid sampling, and formation pressure measurement. Examples of logging include, but are not limited to acoustic logging, temperature logging, noise logging, nuclear logging, density logging, geochemical logging, porosity logging, NMR logging, mud logging, sonic logging, induction logging, micro-resistivity logging, and fluid capacitance logging.

Logging may be carried out with a well logging tool, which refers to a type of device that measures one or more properties of a well versus depth and/or time. In one embodiment, logging is carried out when a well logging tool is moved downward along a wellbore. In one embodiment, logging is carried out when a well logging tool is moved upward to the surface of a wellbore. In one embodiment, logging is carried out by step-wise moving of a well logging tool. The step-wise moving refers to a movement, where the well logging tool moves to a location and stays stationary for a period of time at that location, and then moves to a different location. The period of time may be in the range of 0.1-100 min, or preferably 1-20 min, or preferably 1-5 min.

The thickness profile 302 as used herein refers to a thickness log versus depth of the wellbore. In one embodiment, the thickness profile 302 shows the thickness of the casing and/or the thickness of the tubing versus the depth of the well. In one embodiment, the thickness is measured and recorded by a thickness measurement device. Exemplary thickness measurement devices include, but are not limited to mechanical calipers, flux-leakage tools, ultrasonic calipers, and electromagnetic calipers. The thickness measurement device may be attached to a well logging tool. The thickness measurement device may be secured on an external wall surface of the well logging tool. The thickness measurement device may also be secured inside the well logging tool.

Calipers may be used to identify changes in casing and/or tubing diameter or thickness to indicate existence of wear and/or corrosion 203. Calipers may also be used to monitor casing or tubing deformation. There are three types of calipers based on the measurement protocol; mechanical calipers, ultrasonic calipers, and electromagnetic calipers.

A mechanical caliper is a device for measuring internal diameter of the casing or tubing of a wall by physical movements, for example, by measuring movements of a plurality of arms. One example of mechanical calipers is multi-finger calipers, wherein small changes of internal diameter in casing or tubing can be detected using a large number of arms, or fingers, attached to the multi-finger caliper. The mechanical caliper may be employed to detect deformations, buildup of scale, and/or metal loss due to corrosion 203.

An ultrasonic caliper is a device for measuring internal diameter and/or thickness of the casing or tubing using high-frequency acoustic signals. The ultrasonic gauge emits a high-frequency pulse that is reflected back to the ultrasonic gauge by the casing or tubing wall. The internal diameter of the casing or tubing can be determined from travel time of the pulses. Casing thickness may also be measured by analysis of casing resonance signal, or by detecting separately the pulses' echoes from inner and outer casing surfaces. In one embodiment, the measurement of internal diameter and/or thickness of the casing and/or tubing may be used to detect deformations, buildup of scales, and/or metal loss due to corrosion 203. Amplitude of the pulses' echoes from inner surface of the casing may provide qualitative information on state of the inner surface, such as corrosion or rugosity.

Inside diameter and/or thickness of the casing or tubing may also be measured using an electromagnetic caliper. In the electromagnetic caliper, a coil inside the casing generates an alternating magnetic field. Another coil, which is located farther up the electromagnetic caliper, measures a phase shift introduced by the casing. This phase shift depends on the casing thickness and internal diameter, as well as the casing conductivity and magnetic permeability. The phase shift changes at different frequencies, therefore, by varying the frequency, the thickness and internal diameter can be determined.

Flux leakage tool refers to a device that uses a strong magnetic field to identify and quantify localized corrosion on both inner and outer surfaces of the casing or tubing.

Location of damage as used herein may refer to a region in a wellbore, wherein an imperfection, deformation, and/or distortion in the shape of the casing or tubing of a well is detected. The region may be in the range of 0.1-1 m, or preferably 0.1-0.5 m, or preferably 0.1-0.4 m, or preferably 0.1-0.3 m, or preferably 0.1-0.2 m, below and above the center of the damage in the casing or tubing. The imperfection, deformation, and/or distortion in the shape of the casing or tubing may be detected by comparing the thickness in the thickness profile 302 with a predetermined thickness threshold. The location of damage may be determined by a mechanical caliper, a flux-leakage tool, an ultrasonic caliper, and/or an electromagnetic caliper. Vicinity of the damage also refers to a localized section of the casing or the tubing wherein the damage exists, however, the localized section of the casing or the tubing may have a length in the range of 0.1-20 m, or preferably 0.5-15 m, or preferably 0.5-10 m, or preferably 0.5-5 m, wherein the damage is located in a middle of the localized section. In one embodiment, the localized section has a length of 10 m, wherein the damage is located in the length of 5 m. In this embodiment, the vicinity of the damage has a length of 10 m, whereas the location of the damage may be 0.1-1 m, or preferably 0.1-0.5 m, or preferably 0.1-0.4 m, or preferably 0.1-0.3 m, or preferably 0.1-0.2 m, below and above the center of the damage.

The integrated method further involves logging temperature along the depth of the well to obtain a temperature log 205. Temperature log as used here in refers to a record of temperature along the depth of the well. In one embodiment, the temperature is measured and recorded by at least one temperature sensor. Exemplary temperature sensors include, but are not limited to a thermocouple, a resistance temperature detector, a thermistor, and a silicon bandgap temperature sensor. The temperature sensor may be secured on the well logging tool. In one embodiment, the temperature sensor can measure a temperature in the range of −200-2,000° C., or preferably −100-1,500° C., or preferably 0-1,000° C., or preferably 20-500° C., or preferably 20-200° C.

In one embodiment, the well logging tool may be moving downward for logging to prevent disturbing fluids in the well. The logging may be performed at a constant logging speed. In one embodiment, the constant logging speed is in the range of 0.1-10 m/min, or preferably 1-9 m/min, or preferably 2-6 m/min.

The integrated method further involves logging sound frequency along the depth of the well to obtain a noise log 202. The well logging tool may record/measure downhole noise, for example, from gas bubbling up through liquid in the wellbore, or from turbulence caused by high fluid velocity, sudden pressure reduction, and significant flow vortex. Sound level as used herein may refer to a rate at which sound energy is emitted, reflected, transmitted or received, per unit time. The noise logging may be performed by a submersible noise detector. In one embodiment, the submersible noise detector is a submersible microphone. In one embodiment, the submersible microphone records the sound level and the sound frequency of the signals in a frequency range of 20-50,000 Hz, or preferably 20-30,000 Hz, or preferably 100-30,000 Hz, or preferably 100-20,000 Hz, or preferably 100-10,000 Hz, or preferably 100-5,000 Hz. In one embodiment, the submersible microphone records the sound level in the range of −100-100 dB, or preferably −100-20 dB, or preferably −80-0 dB, or preferably −80-(−20) dB, or preferably −60-(−40) dB, or preferably −60-(−50) dB. In one embodiment, the submersible microphone further records a continuous measurement of the frequency of signals. In one embodiment, the sound frequency of the signals in the noise log may indicate a source of noise and a flow regime, whereas the sound level of the signals may relate to a flow rate in the leak. In one embodiment, the sound level in the noise log is used to determine the location of damage in the casing or the tubing of the wellbore. In one embodiment, the sound level in the noise log is used to determine the type of damage in the casing or the tubing of the wellbore. In one embodiment, the well logging tool may comprise the thickness measurement device, the submersible noise detector, and at least one temperature sensor.

Noise log may refer to a continuous record of the sound level and the sound frequency measured at different positions in the wellbore. Since fluid turbulence may generate sound, high noise amplitude may indicate locations of greater turbulence such as leaks, channels and perforations. In one embodiment, the noise log is also used for detecting channels, measuring flow rates, identifying open perforations, detecting sand production, and/or locating gas-liquid interfaces. In one embodiment, the noise log is a log of a cumulative sound level over all measurable frequencies. In one embodiment, the noise log is a log of a cumulative sound level over a single frequency. In one embodiment, the noise log is a log of a cumulative sound level over a plurality of selected frequency ranges. Different frequency ranges may indicate different sources of noise or different flow regimes.

An integrated method as used herein refers to a method, wherein the thickness profile, the temperature log, and the noise log are used concurrently to determine location and type of damage in casing or tubing of a wellbore. In one embodiment, an integrated formula is used to qualitatively determine the type of damage in the casing or tubing of the wellbore. Data from the thickness profile, the temperature log, and the noise log may be plugged into the integrated formula and the output number may be compared with an integrated threshold value to determine the type of damage in the casing or tubing of the wellbore. In one embodiment, the thickness profile, the temperature log, and the noise log in the integrated formula have different weighting. In one embodiment, the integrated formula is $A \cdot t + B \cdot T + C \cdot f = K/z$, where A is a weighting coefficient for the thickness (t) at the depth (z), B is a weighting coefficient for the temperature (T) at the depth (z), C is the weighting coefficient for the noise frequency (f) at the depth (z), and K is the integrated threshold value. z may also refer to the logging length for the directional wells. Values of A may be in the range of 0-1, or preferably 0.5-1, or preferably 0.8-1, or preferably 0.9-1. Values of B may be in the range of 0-1, or preferably 0.1-1, or preferably 0.2-1, or preferably 0.3-1, or preferably 0.4-1, or preferably 0.5-1, or preferably 0.6-1, or preferably 0.7-1, or preferably 0.8-1, or preferably 0.9-1. Values of C may be in the range of 0-1, or preferably 0.0001-0.5, or preferably 0.001-0.4, or preferably 0.001-0.3, or preferably 0.001-0.2, or preferably 0.001-0.1. In one embodiment, the integrated threshold value (K) is a dimensionless number, which may be in the range of 0-50,000, or preferably 10-1,000, or preferably 10-500, or preferably 10-100. In one embodiment, status of the casing or tubing can be characterized from the integrated threshold value (K). In one embodiment, the integrated threshold value (K) represents endurance and durability of the casing or tubing. In one embodiment, the integrated threshold value for the casing is different than the integrated threshold value for the tubing.

The integrated method further involves determining the location of the damage by identifying a depth in the thickness profile 302 where the thickness is less than a predetermined thickness threshold. Determining the location of the damage as used herein refers to a process of comparing the thickness in the thickness profile 302 of the casing or tubing with the predetermined thickness threshold. In one embodiment, a depth in the thickness profile 302 is identified as the location of the damage, when the thickness in the thickness profile 302 of the casing or tubing at that depth is less than the predetermined thickness threshold. In one embodiment, a depth in the thickness profile 302 is identified as undamaged, when the thickness in the thickness profile 302 of the casing or tubing at that depth is greater than or equal to the predetermined thickness threshold.

In one embodiment, the predetermined thickness threshold for the tubing is the same as the predetermined thickness threshold for the casing. In one embodiment, the predetermined thickness threshold for the tubing is different than the predetermined thickness threshold for the casing. In one embodiment, the predetermined thickness threshold is at least 30%, or at least 40%, or at least 50%, or at least 60%, or at least 70%, or at least 80%, or at least 90%, or at least 95%, or at least 97%, or at least 99%, or at least 99.5% of the initial thickness of the casing or the tubing. In one embodiment, the initial thickness of the casing is in the range of 1-40 mm, or preferably 5-40 mm, or preferably 5-30 mm, or preferably 5-20 mm, wherein the predetermined thickness threshold is at least 30%, or at least 40%, or at least 50%, or at least 60%, or at least 70%, or at least 80%, or at least 90%, or at least 95% of the initial thickness of the casing. In one embodiment, the initial thickness of the tubing is in the range of 1-30 mm, or preferably 3-30 mm, or preferably 3-20 mm, or preferably 4-10 mm, wherein the predetermined thickness threshold is at least 50%, or at least 60%, or at least 70%, or at least 80%, or at least 90%, or at least 95% of the initial thickness of the tubing.

In one embodiment, a caliper log may be used to determine the location of the damage in the casing or in the tubing. Caliper log refers to a continuous record of internal diameter along the depth of a wellbore. Similar to the thickness profile, caliper log can be measured with mechanical calipers, ultrasonic calipers, electromagnetic calipers, and/or flux-leakage tools. In one embodiment, a caliper log may be used to determine a volume of a section of a casing or tubing. In one embodiment, a caliper log may be used to determine a volume of a wellbore or a lateral.

The integrated method further involves determining the type of the damage by comparing the temperature log 205 to a geothermal temperature log 204, and the sound frequency at the damage with a frequency threshold. The types of the damage that can be characterized with this integrated method include, but not limited to corrosion 203 and leak 303. Geothermal temperature log 204 is a characteristic of a wellbore which refers to an intrinsic temperature log (i.e. without presence of a disturbance) along the depth of the wellbore. A geothermal temperature log may be obtained by integrating a geothermal gradient over the depth of the wellbore. Geothermal gradient refers to a rate of increase in temperature per unit depth in the Earth. Although the geothermal gradient may vary from place to place, it is usually in the range of 10-40° C./km, or preferably 20-30° C./km, or preferably 25-30° C./km.

The frequency threshold as used herein refers to an arbitrary threshold value that may be used to determine if the damage in the casing or tubing of the wellbore is corrosion 203 or leak 303. In one embodiment, the frequency threshold is the maximum recorded frequency in the noise log 202 divided by two. In one embodiment, the frequency threshold is at least the maximum recorded frequency in the noise log 202 divided by two. In one embodiment, the frequency threshold is in the range of 0.1-50 KHz, or preferably 0.1-30 KHz, or preferably 0.1-20 KHz, or preferably 1-15 KHz, or preferably 5-15 KHz.

In one embodiment, the damage is determined to be a leak 303, when the temperature of the temperature log 205 is constant or decreases relative to the geothermal temperature log 204 with increasing depth along the vicinity of the damage. "Along the vicinity of the damage" as used herein may refer to a case when logging is performed along the length of the localized section wherein the damage is located in the middle of the localized section. A constant temperature log 205 relative to the geothermal temperature log 204 may refer to an embodiment, where true temperature gradient (i.e. gradient of the temperature log) is in the range of −5-5° C./km, or preferably −2-2° C./km, or preferably around 0° C./km, whereas the geothermal gradient is in the range of 10-40° C./km, or preferably 20-30° C./km, or preferably 25-30° C./km. A decreasing temperature log 205 relative to the geothermal temperature log 204 may refer to an embodiment, where the true temperature gradient from the temperature log is in the range of −50-0° C./km, or preferably −20-0° C./km, or preferably −10-0° C./km, or preferably −5-0° C./km, whereas the geothermal gradient is in the range of 10-40° C./km, or preferably 20-30° C./km, or preferably 25-30° C./km.

In one embodiment, the damage is determined to be corrosion 203, when the temperature of the temperature log 205 increases relative to the geothermal temperature log 204 with increasing depth along the vicinity of the damage. An increasing temperature log relative to the geothermal temperature log 204 may refer to an embodiment, where the true temperature gradient from the temperature log 205 is in the range of 0-60° C./km, or preferably 0-40° C./km, or preferably 0-30° C./km, or preferably 0-20° C./km, or preferably 0-10° C./km, or preferably 0-5° C./km, whereas the geothermal gradient is in the range of 10-40° C./km, or preferably 20-30° C./km, or preferably 25-30° C./km.

In one embodiment, the damage is determined to be a leak 303, when the temperature of the temperature log 205 fluctuates with increasing depth along the vicinity of the damage, and the sound frequency in the noise log 202 is greater than or equal to the frequency threshold in the vicinity of the damage. A fluctuating temperature log as used herein may refer to a condition where the true temperature gradient from the temperature log is not a continuous function. Accordingly, a fluctuating temperature log may refer to a condition where temperature of the temperature log 205 is not increasing (as defined herein as an increasing temperature log), or not decreasing (as defined herein as a decreasing temperature log), or not constant (as defined herein as a constant temperature log).

In one embodiment, the damage is determined to be corrosion 203, when the temperature of the temperature log 205 fluctuates with increasing depth along the vicinity of the damage, and the sound frequency in the noise log 202 is less than the frequency threshold in the vicinity of the damage.

In one embodiment, the damage has at least one crack and the integrated method further comprises determining the depth of the at least one crack by measuring amplitude and travel time of reflected sonic signals. In one embodiment, the submersible noise detector comprises an acoustic transducer, wherein the acoustic transducer emits a sonic signal. The submersible noise detector may further comprise an acoustic receiver, which detects the reflected sonic signals. Travel time as used herein refers to a duration of the passage of a sonic signal from the acoustic transducer to the acoustic receiver.

In one embodiment, the integrated method is conducted in a rigless operation. In one embodiment, the integrated method is a rigless operation. A rigless operation may refer to a well-intervention operation conducted with equipment and support facilities that precludes requirement for a rig over the wellbore. A rig refers to a machine which is used to drill a wellbore. A rig may be located onshore, which is also called a land rig. An onshore rig may comprise mud tanks, mud pumps, masts, drawworks, rotary tables, drillstrings, and power generators. A rig may also be located offshore, which is also called a marine rig. An offshore rig may have same components as the onshore rig, except a drilling platform. While the integrated method may be a rigless operation (i.e. no drilling rig is present), other equipment relating to logging and lowering measurement equipment into the wellbore may still be present.

In one embodiment, the integrated method is conducted on an offshore (i.e. marine) well. In one embodiment, the integrated method is conducted on an onshore (i.e. land) well.

In one embodiment, after the integrated method is used to determine the presence, location, and/or type of damage in a drilling operation, a viscous gel is injected to the vicinity of the damage to prevent any source of leak and to impede severe damage to the casing or tubing. The viscous gel may be a polymer gel. In one embodiment, cement is injected to the vicinity of the damage to prevent any source of leak and to impede severe damage to the casing or tubing.

According to a second aspect, the present disclosure relates to a non-transitory computer readable medium having instructions stored therein that, when executed by a computer, cause the computer to perform an integrated method of determining location and type of a damage in a casing of a well, the integrated method involves logging thickness of the casing along the depth of the well to obtain a thickness profile 302, logging temperature along the depth of the well to obtain a temperature log 205, logging sound level and sound frequency along the depth of the well to obtain a noise log 202, determining the location of the damage by identifying a depth in the thickness profile 302 where the thickness is less than a predetermined thickness threshold, determining the type of the damage by comparing the temperature log 205 to a geothermal temperature log 204, and the sound frequency at the damage with a frequency threshold.

Referring now to FIG. 1. A flowchart of the non-transitory computer readable medium (i.e. an integrated model) for determining location and type of a damage in a casing or tubing of a well is depicted in FIG. 1. The first step 102 is to get the thickness profile with the thickness measurement device.

The second step 103 is to compare each of the thicknesses in the thickness profile with the predetermined thickness threshold. If a thickness at a depth is greater than or equal to the predetermined thickness threshold, then go to the third step 104, which is to identify that the casing or tubing at that depth is in good condition. If the thickness is less than the predetermined thickness threshold, then identify that depth as the damage zone and go to the fourth step 105.

The fourth step 105 is to measure the temperature in the vicinity of the damage zone using one or more of the temperature sensors to get the true temperature gradient.

The fifth step 106 is to determine whether the temperature log in the vicinity of the damage zone is increasing, constant, decreasing or fluctuating/irregular with increasing depth. The fifth step 106 may be determined from the true temperature gradient.

If the temperature log is increasing with increasing depth in the vicinity of the damage zone, then go to the sixth step 107, which is to identify that the damage in the damage zone is corrosion. If the temperature log is decreasing, or constant with increasing depth in the vicinity of the damage zone, then go to the seventh step 108, which is to identify that the damage in the damage zone is leak. If the temperature log is fluctuating/irregular with increasing depth in the vicinity of the damage zone, then go to the eighth step 109.

The eighth step 109 is to measure the sound frequency in the damage zone using the submersible noise detector.

The ninth step 110 is to compare the measured sound frequency in the damage zone with the frequency threshold. If the measured sound frequency is greater than or equal to the frequency threshold, then go to the seventh step 108, which is to identify that the damage in the damage zone is leak. If the measured sound frequency is less than the frequency threshold, then go to the sixth step 107, which is to identify that the damage in the damage zone is corrosion.

In one embodiment, the thickness profile, the temperature log, and the noise log are measured in parallel in real-time. Real-time data refers to a signal that is delivered immediately after collection.

Figure 4:
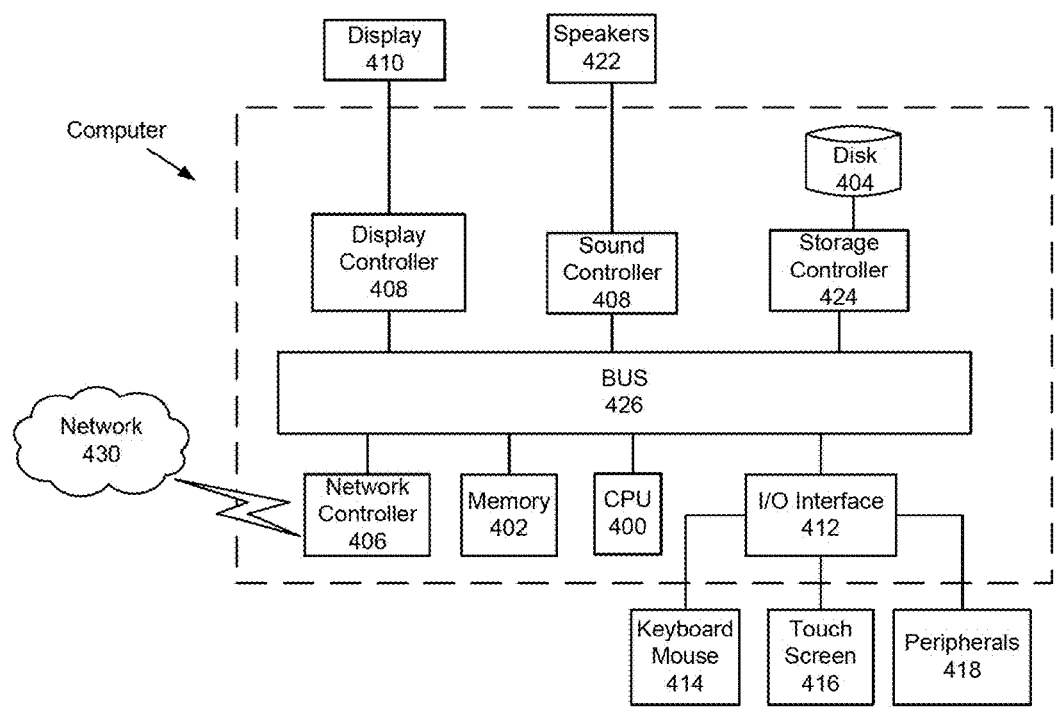
FIG. 4 represents a hardware description of the computer according to exemplary embodiments.

Next, a hardware description of the computer according to exemplary embodiments is described with reference to FIG. 4. In FIG. 4, the computer includes a CPU 400 which performs the processes described above/below. The process data and instructions may be stored in memory 402. These processes and instructions may also be stored on a storage medium disk 404 such as a hard drive (HDD) or portable storage medium or may be stored remotely. Further, the claimed advancements are not limited by the form of the computer-readable media on which the instructions of the inventive process are stored. For example, the instructions may be stored on CDs, DVDs, in FLASH memory, RAM, ROM, PROM, EPROM, EEPROM, hard disk or any other information processing device with which the computer communicates, such as a server or computer.

Further, the claimed advancements may be provided as a utility application, background daemon, or component of an operating system, or combination thereof, executing in conjunction with CPU 400 and an operating system such as Microsoft Windows 7, UNIX, Solaris, LINUX, Apple MAC-OS and other systems known to those skilled in the art.

The hardware elements in order to achieve the computer may be realized by various circuitry elements, known to those skilled in the art. For example, CPU 400 may be a Xenon or Core processor from Intel of America or an Opteron processor from AMD of America, or may be other processor types that would be recognized by one of ordinary skill in the art. Alternatively, the CPU 400 may be implemented on an FPGA, ASIC, PLD or using discrete logic circuits, as one of ordinary skill in the art would recognize. Further, CPU 400 may be implemented as multiple processors cooperatively working in parallel to perform the instructions of the inventive processes described above.

The computer in FIG. 4 also includes a network controller 406, such as an Intel Ethernet PRO network interface card from Intel Corporation of America, for interfacing with network 430. As can be appreciated, the network 430 can be a public network, such as the Internet, or a private network such as an LAN or WAN network, or any combination thereof and can also include PSTN or ISDN sub-networks. The network 430 can also be wired, such as an Ethernet network, or can be wireless such as a cellular network including EDGE, 3G and 4G wireless cellular systems. The wireless network can also be WiFi, Bluetooth, or any other wireless form of communication that is known.

The computer further includes a display controller 408, such as a NVIDIA GeForce GTX or Quadro graphics adaptor from NVIDIA Corporation of America for interfacing with display 410, such as a Hewlett Packard HPL2445w LCD monitor. A general purpose I/O interface 412 interfaces with a keyboard and/or mouse 414 as well as a touch screen panel 416 on or separate from display 410. General purpose I/O interface also connects to a variety of peripherals 418 including printers and scanners, such as an OfficeJet or DeskJet from Hewlett Packard.

A sound controller 420 is also provided in the computer, such as Sound Blaster X-Fi Titanium from Creative, to interface with speakers/microphone 422 thereby providing sounds and/or music.

The general purpose storage controller 424 connects the storage medium disk 404 with communication bus 426, which may be an ISA, EISA, VESA, PCI, or similar, for interconnecting all of the components of the computer. A description of the general features and functionality of the display 410, keyboard and/or mouse 414, as well as the display controller 408, storage controller 424, network controller 406, sound controller 420, and general purpose I/O interface 412 is omitted herein for brevity as these features are known.

The examples below are intended to further illustrate protocols for determining location and type of a damage in casing or tubing of a wellbore from thickness profile, temperature log, and noise log and are not intended to limit the scope of the claims.

Example 1

For downhole leak identification in oil, gas and water wells three aims were set. The first aim is to obtain different types of logs in order to find a new integrated approach. The second aim is to use the integrated method to detect downhole leaks by utilizing only rigless data based on full interpretation and evaluation of different logs in the field: temperature, noise, and thickness log. Finally, the last aim is to compare rigless approach results with conventional rig approach results for downhole leak detection.

Example 2

The developed integrated model is used to detect the downhole leak through analyzing only the numerical log data of corrosion, temperature and noise surveys. Based on the developed model, some instructions were implemented to allow the program decided that the completion in a specific depth is either leaked or only corroded or in a good condition. These rules were put based on these following surveys and in a specific order:

For corrosion survey, a corrosion factor was set such that, for a 4½" tubing, 53% corrosion factor was implemented to the original tubing thickness which will indicate the presence of either corrosion or leak. If corrosion sigma (i.e. measured thickness) in a specific depth is less than 53% of the original tubing thickness, then the model highlights this location for more investigations by performing a temperature survey.

For a 7" casing, 39% corrosion factor from the original thickness was implemented to the original casing thickness which will indicate the presence of either corrosion or leak. If corrosion sigma (i.e. measured thickness) in a specific depth is less than 39% of the original casing thickness, then the model highlights this location for more investigations by performing a temperature survey.

Temperature survey was performed on the highlighted locations to indicate the type of the damage in those locations. Accordingly, when the temperature log is constant or decreasing with depth, this is an indication of leak in the highlighted location. However, when the temperature log is increasing with depth, this is an indication of corrosion in the highlighted location. The model ends at this step.

However, when irregularity was observed in the temperature log in the highlighted locations, more investigations were performed by conducting a noise survey.

If the sound frequency in the highlighted location is greater than or equal to the frequency threshold, then there is a leak in the highlighted location. However, if the sound frequency in the highlighted location is less than the frequency threshold, it indicates existence of corrosion in the highlighted location.

Example 3

The results of the developed model verify the conventional rig approach results. However, there is still a minor difference between the developed model and the conventional rig approach results. This difference may be due to accuracy of the results implying that what is predicted by the developed model is often more accurate than a manual prediction. The maximum noticed frequency in a well was 18 KHz and the minimum was zero. So, our reference noise frequency (i.e. the frequency threshold) is 9 KHz. In this case, if the frequency in a specific depth is greater than or equal to 9 KHz, this will confirm the presence of leak only if it is supported by the presence of damage from the thickness profile and the temperature log.

Example 4

Figure 2:
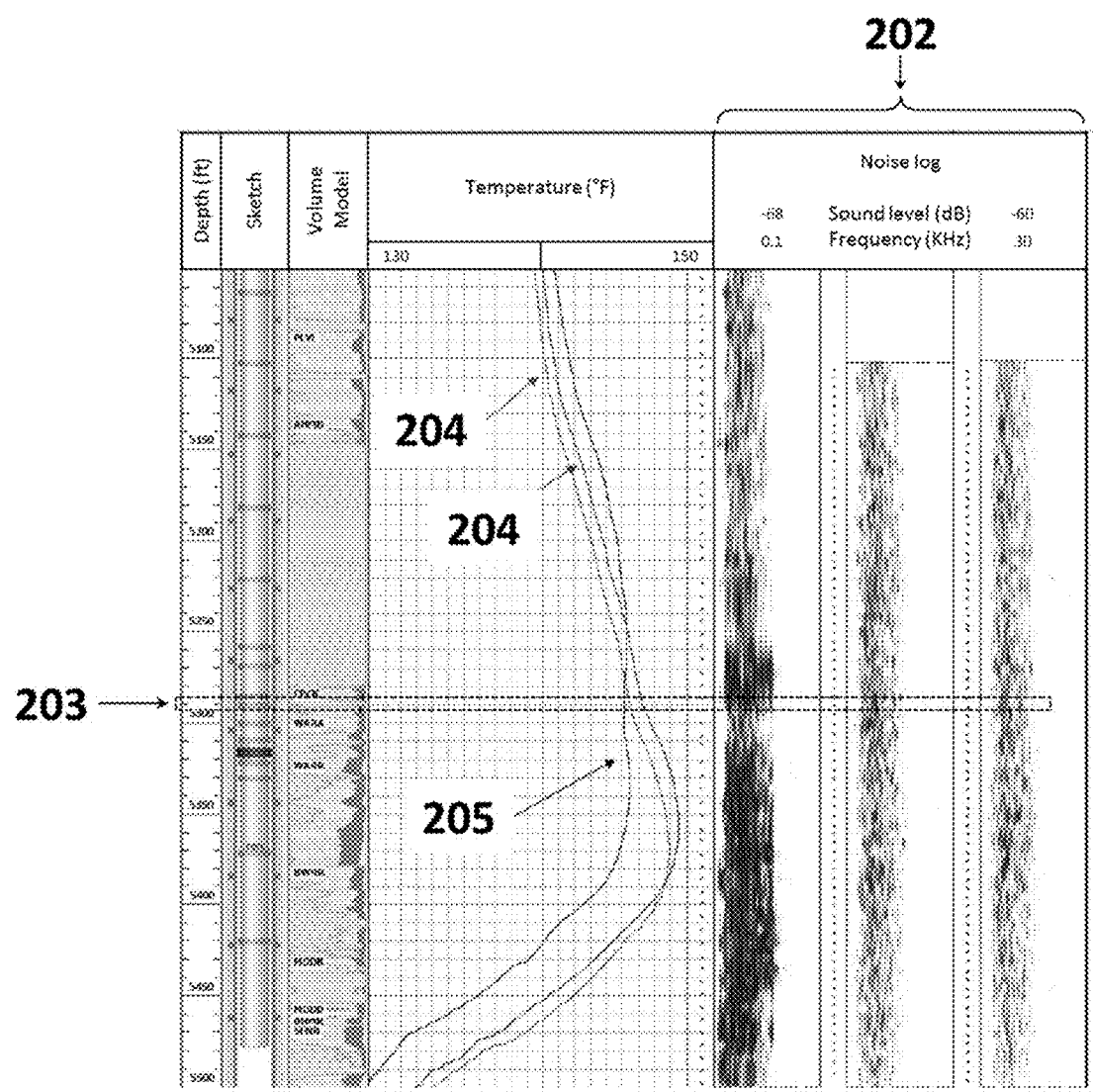
FIG. 2 depicts an integrated noise log and temperature log versus depth of a well.

At depth of 5290 ft which is slightly above the packer as in FIG. 2, damage was noticed as the measured casing thickness was 0.234 inch, while the actual casing thickness was 0.634 inch. The damage was corrosion as verified by irregularities observed in both noise and temperature surveys. The noise was due to packer not sealing well in that depth while the decreasing temperature in the temperature log was due to a prolonged injection in the same formation.

Example 5

Figure 3:
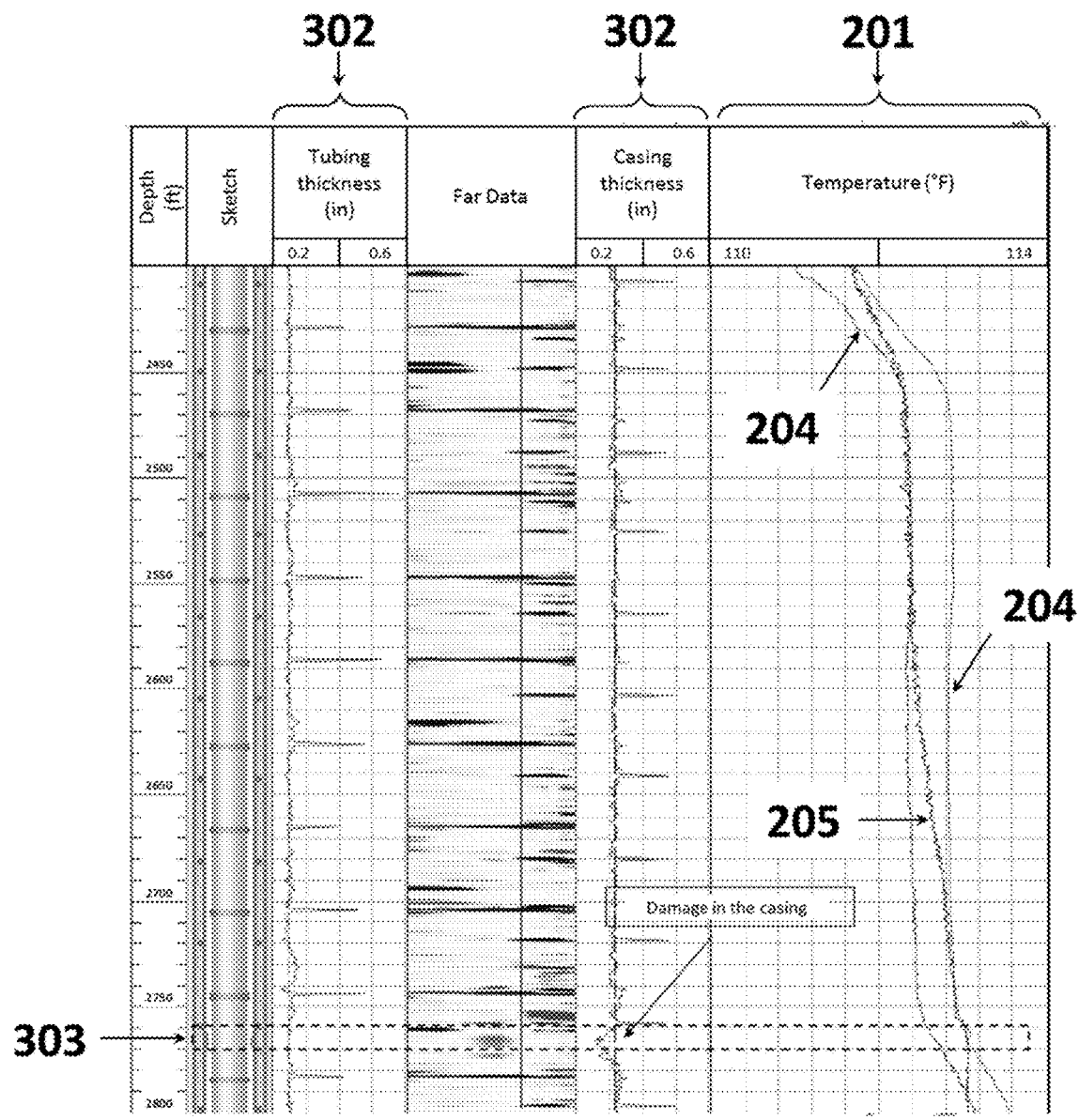
FIG. 3 depicts an integrated tubing thickness profile, casing thickness profile, and temperature log versus depth of a well.

At a depth of 2763 ft as in FIG. 3, damage was detected since the measure tubing thickness was 0.27 inch while the actual tubing thickness was 0.542 inch. After checking the temperature log, it was noticed that temperature was relatively constant with increasing depth which was an indication of tubing leakage at the damage. The frequency in the noise log at that depth was 9 KHz which also support the presence of tubing leakage at the damage. The damage location was confirmed by conventional rig approach in addition to this developed model.

Example 6

Based on the temperature log, the noise log, and the thickness log the integrated method identified the leakage zones through the integrated model. The obtained results from the rigless integrated method were identical to the results from the conventional rig approach. The integrated method seems to be more reliable compared to the conventional rig approach since it can identify not only the leak zones but also corrosion damage zones, whereas the conventional rig approach can only identify the leak zones. The inventive method appears to have both practical and commercial values due to the simplicity of implementation and reliability in determining the location and type of a damage in casing or tubing of a wellbore.

The invention claimed is:

1. An integrated method of determining and repairing damage in a casing of a well, comprising:
    logging thickness of the casing along the depth of the well to obtain a thickness profile using a thickness measurement device selected from the group consisting of an ultrasonic caliper and an electromagnetic caliper;
    logging temperature along the depth of the well to obtain a temperature log;
    logging sound frequency along the depth of the well to obtain a noise log;
    determining a location of the damage by identifying a depth in the thickness profile where the thickness is less than a predetermined thickness threshold;
    determining the type of the damage by comparing the temperature log to a geothermal temperature log, and the sound frequency at the damage with a frequency threshold; and
    injecting a polymer gel to the vicinity of the damage to repair the damage,
    wherein the damage is determined to be a leak, when the temperature of the temperature log is constant or decreases relative to the geothermal temperature log with increasing depth along the vicinity of the damage, and
    wherein the damage is determined to be corrosion, when the temperature of the temperature log increases relative to the geothermal temperature lou with increasing depth along the vicinity of the damage.

2. The integrated method of claim 1, wherein the damage is determined to be a leak, when the temperature of the temperature log fluctuates with increasing depth along the vicinity of the damage, and the sound frequency is greater than or equal to the frequency threshold in the vicinity of the damage.

3. The integrated method of claim 1, wherein the damage is determined to be corrosion, when the temperature of the temperature log fluctuates with increasing depth along the vicinity of the damage, and the sound frequency is less than the frequency threshold in the vicinity of the damage.

4. The integrated method of claim 1, wherein the damage has at least one crack and the method further comprises determining the depth of the at least one crack by measuring amplitude and travel time of reflected sonic signals in the vicinity of the damage.

5. The integrated method of claim 1, wherein the temperature is logged by at least one temperature sensor selected from the group consisting of a thermocouple, a resistance temperature detector, a thermistor, and a silicon bandgap temperature sensor.

6. The integrated method of claim 1, wherein the noise log further comprises sound level, and the sound level and the sound frequency in the noise log are obtained by a submersible noise detector.

7. The integrated method of claim 1, wherein the casing is selected from the group consisting of a conductor casing, a surface casing, an intermediate casing, and a production casing.

8. The integrated method of claim 1, which is a rigless operation.

* * * * *